US00PP36248P2

(12) United States Plant Patent
Eggleton

(10) Patent No.: US PP36,248 P2
(45) Date of Patent: Nov. 12, 2024

(54) ***HEBE* PLANT NAMED 'IB 605-2'**

(50) Latin Name: ***Hebe* hybrid**
Varietal Denomination: IB 605-2

(71) Applicant: Steven Eggleton, Victoria (AU)

(72) Inventor: Steven Eggleton, Victoria (AU)

( * ) Notice: Subject to any disclaimer, the term of this patent is extended or adjusted under 35 U.S.C. 154(b) by 0 days.

(21) Appl. No.: 18/589,600

(22) Filed: Feb. 28, 2024

(51) Int. Cl.
*A01H 5/02* (2018.01)
*A01H 6/68* (2018.01)

(52) U.S. Cl.
USPC ..... Plt./251
CPC ..... *A01H 6/68* (2018.05)

(58) Field of Classification Search
USPC ..... Plt./251
CPC ..... A01H 5/02
See application file for complete search history.

*Primary Examiner* — Kent L Bell
(74) *Attorney, Agent, or Firm* — Penny J. Aguirre

(57) ABSTRACT

A new cultivar of *Hebe* plant named 'IB 605-2' that characterized by its strong anthocyanin coloration on new leaf growth, its flowers that is are mauve pink in color, its compact and dense plant habit, and its small to medium sized leaves.

3 Drawing Sheets

Botanical classification: *Hebe* hybrid.
Cultivar designation: 'IB 605-2'.

BACKGROUND OF THE INVENTION

The present invention relates to a new and distinct *Hebe* plant, botanically of hybrid origin and known as *Hebe* 'IB 605-2' and will be referred to hereafter by its cultivar name, 'IB 605-2'. 'IB 605-2' is an evergreen shrub grown for use as a container plant and as a landscape shrub.

The new cultivar of *Hebe* arose from a breeding program conducted by the Inventor in Wonga Park, Victoria, Australia with the goal of developing new *Hebe* cultivars with compact plant habits, anthocyanin coloration in the foliage and floriferous blooming habits in a range of flower colors. The Inventor made a cross in August of 2015 between *Hebe* cultivars 'Black Beauty' (not patented) as the female parent and 'Pretty in Pink' (not patented) as the male parent. The Inventor selected 'IB 605-2' in May of 2016 as a single unique plant from amongst the seedlings that resulted from the above cross.

Asexual propagation of the new cultivar was first accomplished by stem cuttings in November of 2016 by the Inventor in Wonga Park, Victoria, Australia. Asexual propagation by stem cuttings has determined that the characteristics of the new cultivar are stable and reproduced true to type in successive generations.

SUMMARY OF THE INVENTION

The following traits have been repeatedly observed and represent the characteristics of the new cultivar, which in combination distinguish 'IB 605-2' as a new and distinct cultivar of *Hebe*.

1. 'IB 605-2' exhibits strong anthocyanin coloration on new leaf growth.
2. 'IB 605-2' exhibits flowers that are mauve pink in color.
3. 'IB 605-2' exhibits a compact and dense plant habit.
4. 'IB 605-2' exhibits small to medium sized leaves.

The female parent plant of 'IB 605-2' differs from 'IB 605-2' in having a taller plant height, a less floriferous blooming habit, and stronger anthocyanin coloration on the foliage. The male parent plant of 'IB 605-2' differs from 'IB 605-2' in having a shorter plant height and stronger anthocyanin coloration on the foliage. 'IB 605-2' can be most closely compared to *Hebe* cultivars 'Strawberry Truffle' (not patented) and 'Turkish Delight' (not patented). 'Strawberry Truffle' and 'Turkish Delight' are both similar to 'IB 605-2' in having anthocyanin coloration on new leaf growth and compact plant habits. 'Strawberry Truffle' differs from 'IB 605-2' in having a less floriferous habit and flowers that are deeper pink in color. 'Turkish Delight' differs from 'IB 605-2' in having much more anthocyanin coloration on the foliage, more narrow leaves, and flowers that are purple in color.

BRIEF DESCRIPTION OF THE DRAWINGS

The accompanying color photographs illustrate the overall appearance and distinct characteristics of the new *Hebe*. The photographs were taken of a 1-year-old plant of 'IB 605-2' as grown outdoors and in an unheated greenhouse (overwintered) in a 2-gallon container in Abbotsford, BC, Canada.

The photograph in FIG. 1 provides a side view of 'IB 605-2' in bloom.

Figure 1:
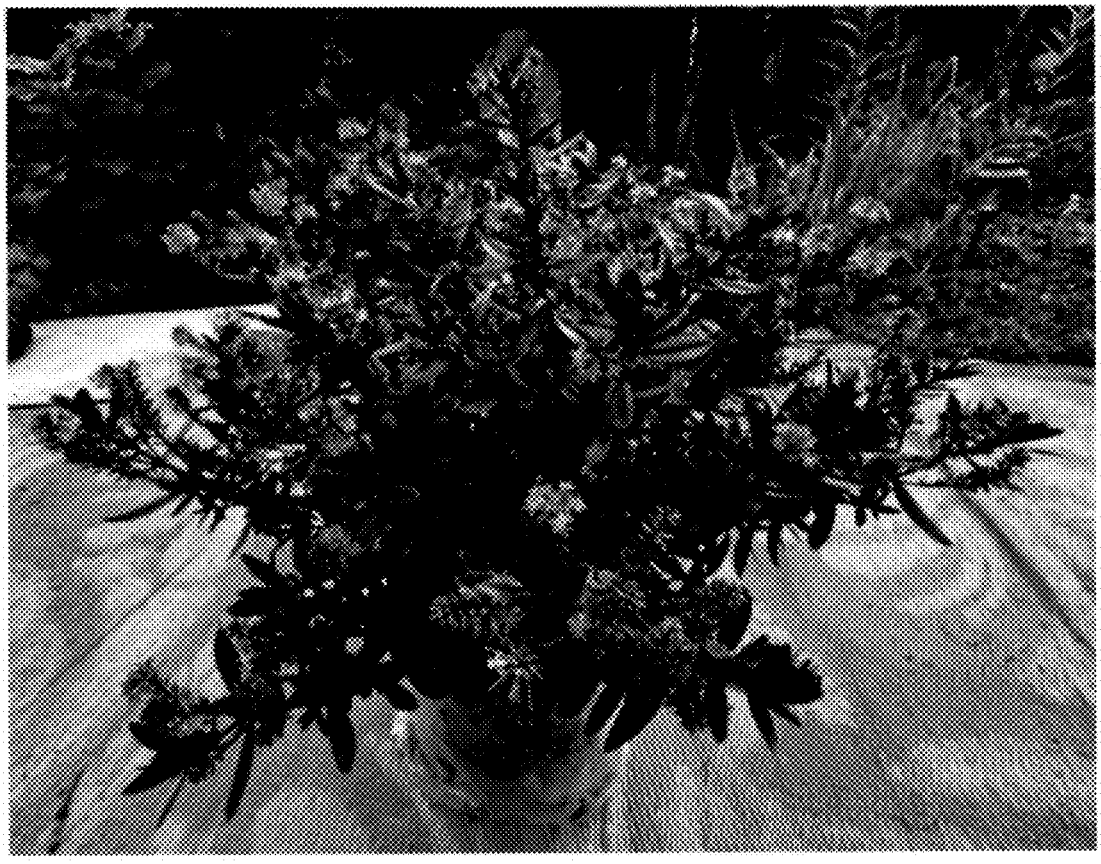
Figure 2:
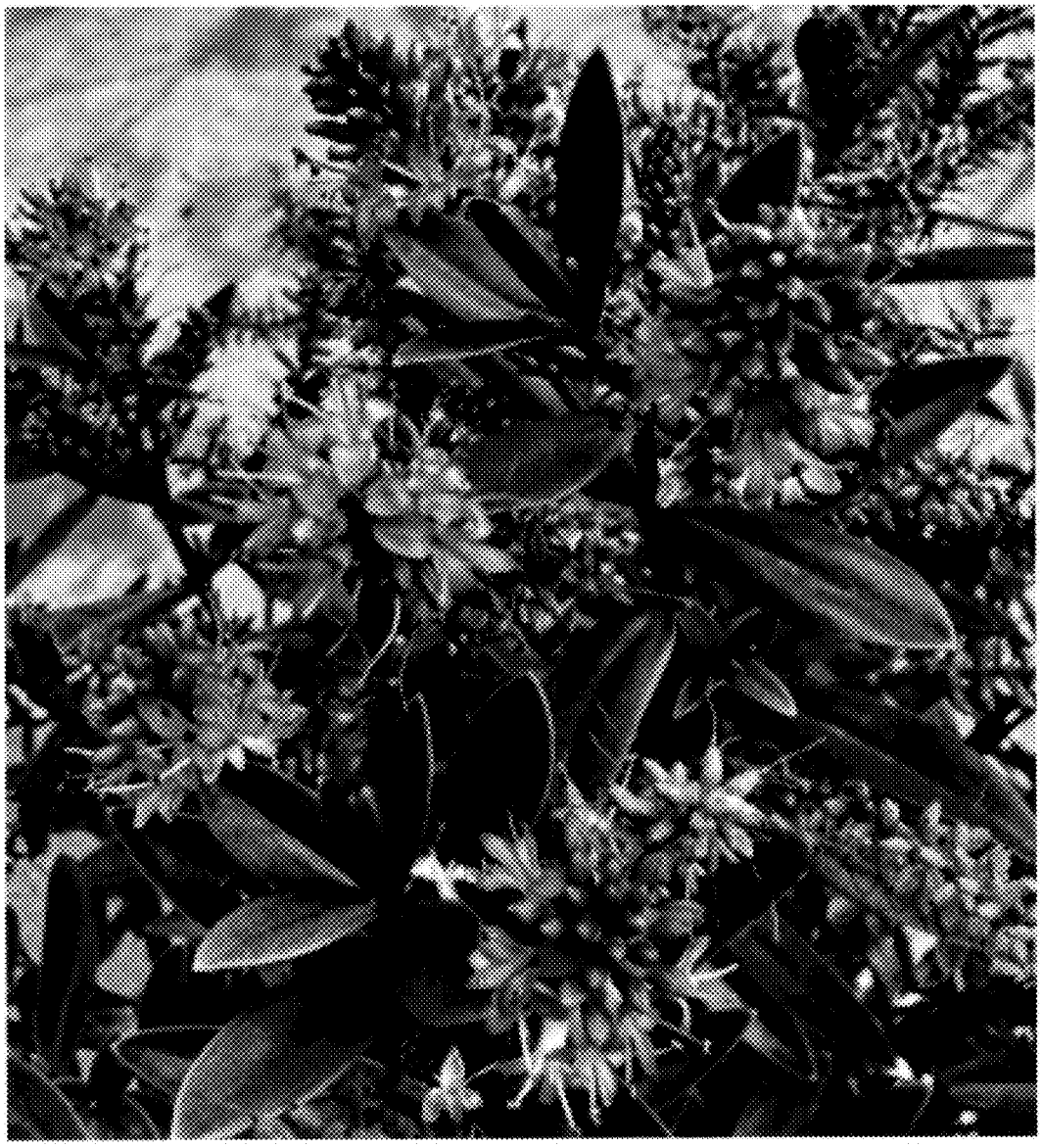

The photograph in FIG. 2 provides a close-up view of the inflorescences of 'IB 605-2'.

Figure 3:
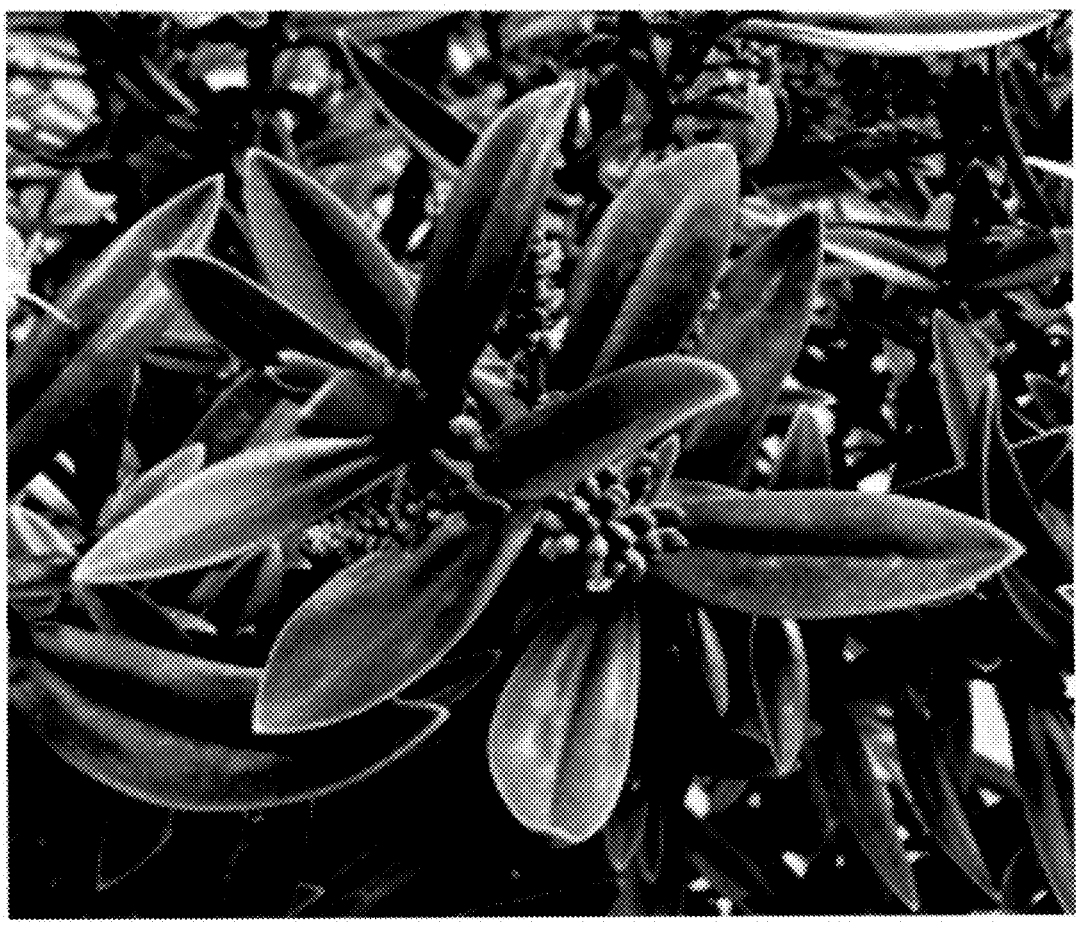

The photograph in FIG. 3 provides a close-up view of the foliage of 'IB 605-2'.

The colors in the photographs may differ slightly from the color values cited in the detailed botanical description, which accurately describe the colors of the new *Hebe*.

DETAILED BOTANICAL DESCRIPTION OF THE PLANT

The following is a detailed description of 1-year-old plants of the new cultivar as grown outdoors and in an unheated greenhouse (overwintered) in 2-gallon containers in Abbotsford, BC, Canada. The phenotype of the new cultivar may vary with variations in environmental, climatic, and cultural conditions, as it has not been tested under all possible environmental conditions. The color determination is in accordance with The 2015 Colour Chart of the Royal Horticultural Society, London, England, except where general color terms of ordinary dictionary significance are used.

General description:

*Blooming period*.—Late spring to late summer in Melbourne, Australia.

*Plant type*.—Evergreen shrub.

*Plant habit*.—Compact, upright-spreading.

*Height and spread*.—Average of 38 cm in height, 57 cm in width as a 23-week-old plant grown in a container, reaches 50 cm in height and 80 cm in width as a mature plant in the landscape.

*Hardiness*.—At least in U.S.D.A. Zones 8 to 11.

*Diseases and pests*.—Has shown some resistance to powdery mildew (typically caused by *Podosphaera fuliginea*).

*Root description*.—Densely fibrous, 164A and 166A.

*Propagation*.—Softwood stem cuttings.

*Root development*.—10 to 14 days for root initiation, 4 to 6 weeks to produce a young rooted plug.

*Growth rate*.—Moderate to vigorous.

Branch description:

*Branch size*.—Main; an average of 8 cm in length and 6 mm in diameter, lateral; an average of 22 cm in length and 4 mm in diameter.

*Branch shape*.—Round.

*Branch color*.—Young; 144A, mature and bark; 197A.

*Branch surface*.—Young; glabrous and glossy, mature and bark; dry, matte and slightly exfoliating.

*Branch strength*.—Strong.

*Internode length*.—Average of 1 cm.

*Branching habit*.—Upright to outward.

*Branching quantity*.—Main; 8, lateral per main branch; 20.

Foliage description:

*Leaf shape*.—Elliptic to narrowly obovate.

*Leaf division*.—Single.

*Leaf base*.—Cuneate.

*Leaf apex*.—Acute.

*Leaf venation*.—Upper surface; only mid-vein visible, some as leaf color and sometimes flushed with N77A, lower surface; inconspicuous.

*Leaf margins*.—Entire.

*Leaf attachment*.—Sessile.

*Leaf arrangement*.—Opposite, whorled.

*Leaf surface*.—Both surfaces glossy, glabrous.

*Leaf color*.—Young upper and lower surface completely flushed with; N77A and N79C, mature upper and lower surface; 137A.

*Leaf number*.—Average of 60 per lateral branch.

*Leaf size*.—An average of 5 cm in length and 1 cm in width.

Flower description:

*Inflorescence type*.—Raceme.

*Inflorescence size*.—Average of 7 cm in height and width.

*Inflorescence lastingness*.—4 to 6 weeks, persistent.

*Flower shape*.—Campanulate.

*Flower fragrance*.—None.

*Flower quantity*.—Average of 300 flowers per inflorescence.

*Flower arrangement*.—Axillary racemes.

*Flower aspect*.—Outward.

*Flower size*.—Average of 7 mm in height, 7 mm in diameter, and 1.2 cm in depth, throat diameter 3 mm, flower tube 3 mm in length and 2 mm in diameter.

*Peduncles*.—Strong, 7 cm in length and about 2 mm in diameter, 144A in color, held outward and upward to lateral branch, surface glossy and glabrous.

*Pedicels*.—Moderate strength, 2 mm in length and about 0.75 mm in diameter, 144A in color, held outward and upward to lateral branch, surface glossy and glabrous.

*Flower buds*.—Linear in shape, 5 mm in length and 2 mm in diameter, surface matte, color; emerging buds N81A, before burst N82A.

*Calyx*.—Rotate-shaped, average of 3.5 mm in length and 2.5 mm in diameter.

*Sepals*.—4, 2 mm in length and 1.5 mm in width, acute apex, base 50% fused, both surfaces matte and 137A in color.

*Petals*.—4, bottom 49% fused, average of 4 mm in length and 2 mm in width, linear and cup-shaped, entire margins, apex rounded, upper and lower surface is smooth, glabrous and velvety with a slight sheen, color: both surfaces when opening and fully open; a blend of 85A and 84A with tips 86B and suffused with NN155C on upper surface as they age, base, tube and throat NN155C.

Reproductive organs:

*Gynoecium*.—Pistil; 1, 6.5 mm in length, stigma; insignificant, style; surface is glossy, young color NN155C, mature color N87B in color, ovary; inferior, round in shape, glossy surface, 140B in color.

*Androecium*.—Stamens; 2, anthers; oblong, dorsifixed, 2 mm in length, 1 mm in width, matte surface, young color 63A, mature color 166A, filaments; 1 cm in length, 1 mm in width, glossy surface, young color N87A, mature color NN155C, pollen; moderate in quantity and11A in color.

*Fruit and seed*.—None observed.

It is claimed:

1. A new and distinct cultivar of *Hebe* plant named 'IB 605-2' as herein illustrated and described.

* * * * *